United States Patent [19]

Matsumura et al.

[11] 4,376,573

[45] Mar. 15, 1983

[54] APPARATUS FOR MEASURING THE REFRACTIVE POWER OF THE EYE

[75] Inventors: Isao Matsumura, Yokosuka; Yasuyuki Ishikawa, Kawaguchi; Shigeo Maruyama, Machida; Reiji Hirano; Yoshimi Kohayakawa, both of Yokohama, all of Japan

[73] Assignee: Canon Kabushiki Kaisha, Tokyo, Japan

[21] Appl. No.: 131,499

[22] Filed: Mar. 18, 1980

[30] Foreign Application Priority Data

Mar. 20, 1979 [JP] Japan .................................. 54-32628

[51] Int. Cl.³ .............................................. A61B 3/10
[52] U.S. Cl. .................................... 351/212; 351/214; 351/237
[58] Field of Search ....................... 351/6, 7, 13, 14, 16

[56] References Cited

U.S. PATENT DOCUMENTS

4,021,102  5/1977  Iizuka ..................................... 351/13

Primary Examiner—John K. Corbin
Assistant Examiner—Rodney Bovernick
Attorney, Agent, or Firm—Fitzpatrick, Cella, Harper & Scinto

[57] ABSTRACT

In an apparatus having a ray generator for directing measuring rays through a first optical path, a light-receiving portion for receiving the measuring rays reflected by the eye fundus through a second optical path, and a uniting device for uniting the first and second optical paths to form a third optical path, and also having movable lens groups in each of the first and second optical paths or a movable lens group in the third optical path, and wherein the movable lens groups or group is moved along the optical path to measure the refractive power of the eye from signals corresponding to the positions of the movable lens groups or group and the signal of the light-receiving portion, the movable lens groups or group is made into an afocal system to prevent the dimensions of the pupil from being varied and a collimator for collimating the principal rays is fixedly disposed on that side of the movable lens groups or group which is adjacent to the eye to be examined.

22 Claims, 33 Drawing Figures

APPARATUS FOR MEASURING THE REFRACTIVE POWER OF THE EYE

BACKGROUND OF THE INVENTION

1. Field of the Invention

This invention relates to an apparatus for measuring the refractive power of the eye. More particularly, it relates to an apparatus for preventing any variation in dimensions of the image of an optical pupil, i.e. the stop of an optical system, or the image of the iris of the eye when an optical system for projecting a measuring beam onto the eye fundus and an optical system for receiving the beam reflected by the eye fundus are focused to the eye fundus.

2. Description of the Prior Art

Eye refractometers have long been used to examine the function of the eye or to obtain data for making spectacles. According to the conventional eye refractometers, a test chart has been projected upon the eye fundus and focus adjustment has been effected while the image of this chart is being observed through the viewfinder so that the eye refraction is measured from the amount of adjustment. In contrast, apparatuses for automatically measuring the eye refraction have recently been proposed in U.S. Pat. Nos. 3,536,383; 3,819,256; 3,883,233 and 3,888,569 and these apparatus are characterized by a beam projecting portion for projecting a beam forming a chart image and a detecting portion for detecting the chart image reflected by the eye fundus.

The assignee of the present invention also has proposed, in U.S. Applications Ser. No. 944,304 and now U.S. Pat. No. 4,293,198 and No. 75,115 (German Application Pat. No. 2937891.4), an apparatus for measuring the refraction error including information on astigmatism. The examples shown in FIGS. 1 and 6 of the accompanying drawings are modifications of the embodiments described in the specifications of said applications.

Figure 1:
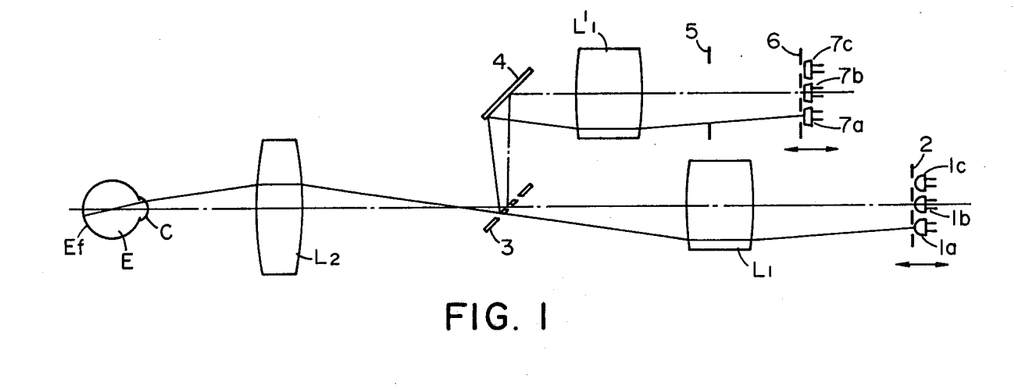
FIG. 1 is a longitudinal cross-sectional view of an embodiment described in the aforementioned application.
Figure 2:
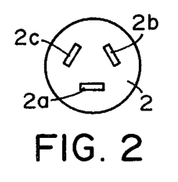
FIGS. 2–5 are plan views of the components in the embodiment of FIG. 1.
Figure 3:
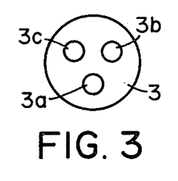
Figure 4:
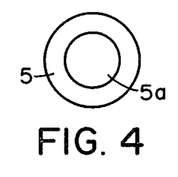
Figure 5:
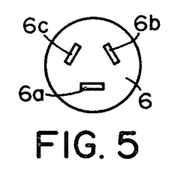
Figure 6:
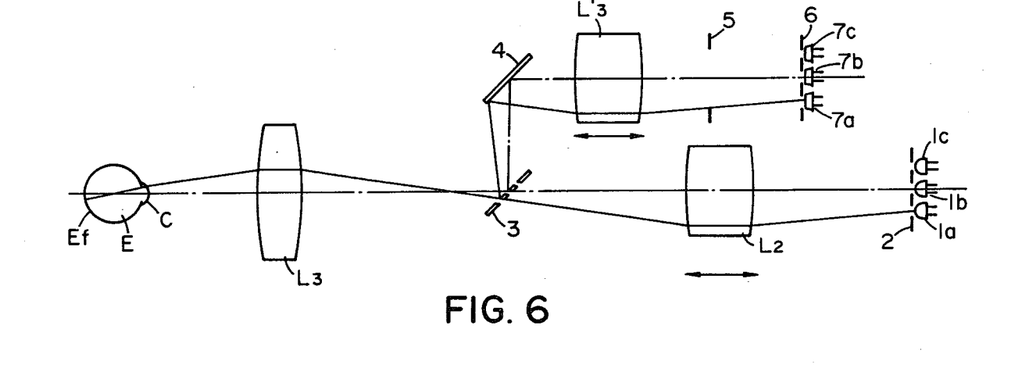
FIG. 6 is a longitudinal cross-sectional view of another embodiment described in the aforementioned application.

Here, the constructions of FIGS. 1 and 6 will first be explained, and then the problems peculiar thereto will be pointed out. FIG. 1 refers to a case where the light-receiving surface is moved. In FIG. 1, reference characters $1a$, $1b$ and $1c$ designate light sources, and reference character 2 denotes a mask having three slits $2a$, $2b$ and $2c$ equidistant from the center thereof and perpendicular to meridians which form 120° with one another, as shown in FIG. 2. The light sources are provided behind the respective slits. $L_1$ designates a fixed lens, 3 an apertured mirror having apertures $3a$, $3b$ and $3c$ equidistant from the center thereof and spaced apart from one another by 120°, as shown in FIG. 3, $L_2$ an objective lens, E the eye to be examined, Ef the eye fundus, C the cornea of the eye, 4 a reflecting member, $L_1'$ a fixed lens similar to $L_1$, 5 an aperture stop having an opening $5a$ as shown in FIG. 4, and 6 a light-receiving mask having slits $6a$, $6b$ and $6c$ as shown in FIG. 5. The slits $2a$ and $6a$, $2b$ and $6b$, and $2c$ and $6c$ are in optically conjugate relationship with respect to the mirror 3. Designated by $7a$, $7b$ and $7c$ are light receptors which can substantially cover the slit portions of the slits $6a$, $6b$ and $6c$, respectively. The light from the light source $1a$ passes through the slit $2a$, the fixed lens $L_1$, the aperture $3a$ of the apertured mirror 3, the objective lens $L_2$ and the cornea C to the eye fundus Ef and forms the image of the slit $2a$ on the eye fundus Ef. The light reflected by the eye fundus Ef passes to the slit $6a$ on the light-receiving mask 6 via the cornea C, the objective lens $L_2$, the apertured mirror 3, the reflecting member 4, the fixed lens $L_1'$ and the aperture stop 5, and is received by the light receptor $7a$. This also holds true with the lights from the light sources $1b$ and $1c$.

When the mask 2 and the light sources $1a$, $1b$, $1c$ and the mask 6 and light receptors $7a$, $7b$, $7c$ are simultaneously moved in one direction in synchronism with one another, the images of the slits $2a$, $2b$, $2c$ formed on the mask 6 which have been blurred at first and positionally deviated in the direction of the diametral line come to exactly overlap with the slits $6a$, $6b$, $6c$ and become clear and exhibit the extremal value of the quantity of light. Although not depicted in FIG. 1, it is to be understood that the amount of movement of the slit 2 is always being detected by position detecting means such as a linear encoder or the like. The position thereof on the optic axis corresponds to the refractive power.

Accordingly, if the apparatus is designed such that the output of the position detecting means is read when the light receptors $1a$, $1b$ and $1c$ have detected the extremal value, it is possible to know the refractive power for each diametral line.

The refractive power of the eye to be examined is found by the use of the output received by the above-described method, and with the refractive powers actually measured with respect to three diametral line directions being defined as $P_1$, $P_2$ and $P_3$, various amounts can be found by the use of the following equation. That is, when use is made of the spherical surface degree number A, the cylinder degree number B and the cylinder axis $\phi$, the equation $P = A + B \sin(2\theta + \phi)$ is established. $\theta$ is the angle of predetermined three diametral lines. Finally, A, B and $\phi$ can be simply evaluated by a calculation from the refractive powers in the three diametral line directions.

In the construction of FIG. 6, lenses movable in the direction of the optic axis are disposed instead of the fixed lenses $L_1$ and $L_1'$ of FIG. 1, and the light sources $1a$, $1b$, $1c$, the masks 2 and 6 and the light receptors $7a$, $7b$, $7c$ are fixed. The lenses $L_3$ and $L_3'$ are once simultaneously moved in one direction during one measurement and, during this one scanning, the light receptors $7a$, $7b$, $7c$ pass through the extremal value and from the positions of the lenses at the time point of the extremal value, there are obtained the refractive powers for the three diametral line directions.

In the optical system as shown in FIG. 1, the opening $5a$ of the aperture stop 5 can always be maintained at a constant magnification in this optical system with respect to the eye E to be examined and therefore, it is possible to eliminate the fluctuation of brightness for diopter variation, but it is necessary to move the light source portion including the mask 2 and the light-receiving portion including the light-receiving mask 6 and the movement of the light source portion and the light-receiving portion is not linearly varied for the diopter variation of the eye to be examined and thus, the movement and correction thereof are cumbersome. On the other hand, in the optical system as shown in FIG. 6, fluctuation of brightness for diopter variation occurs and moreover, the movement of the lenses is not linear.

SUMMARY OF THE INVENTION

It is a primary object of the present invention to improve the accuracy of measurement of the eye refractive power.

It is another object of the present invention to prevent fluctuation of the dimensions of the pupil or fluctuation of brightness when the lens group or groups are moved for measurement.

It is still another object of the present invention to render the amount of variation of the diopter of the eye and the amount of movement of the lens group or groups into a linear relationship.

The invention will become fully apparent from the following detailed description thereof taken in conjunction with the accompanying drawings.

BRIEF DESCRIPTION OF THE DRAWINGS

FIGS. 22–25A and 25B are plan views of the components in the embodiment of FIG. 21.

DESCRIPTION OF THE PREFERRED EMBODIMENTS

Figure 7:
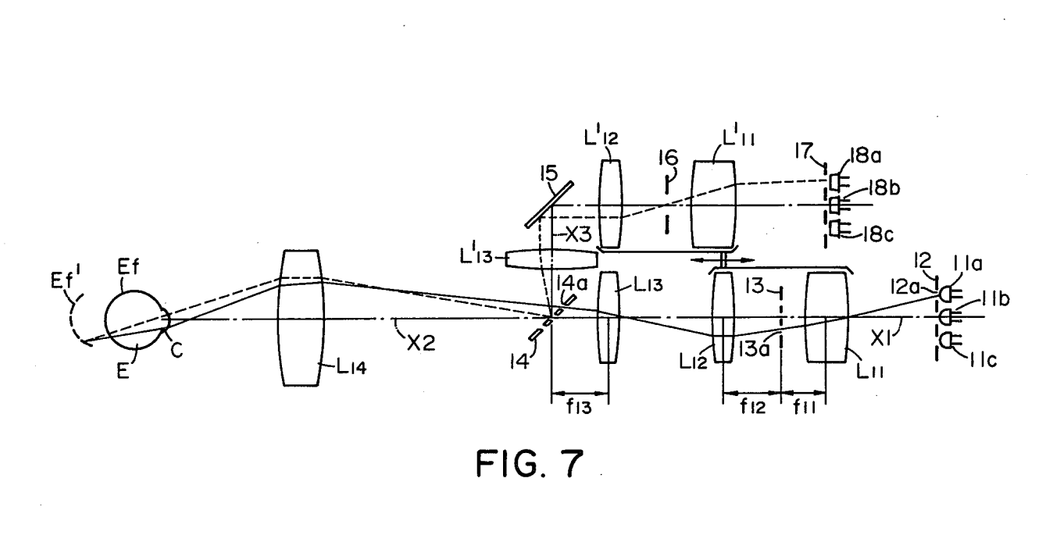
FIG. 7 is a longitudinal cross-sectional view of a first embodiment of the present invention.
Figure 8:
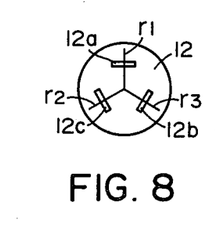
FIGS. 8–12 are plan views of the components in the embodiment of FIG. 7.
Figure 9:
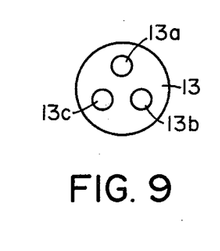
Figure 10:
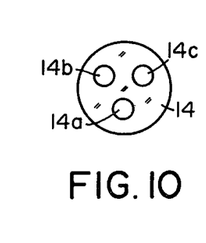

In FIG. 7 which shows a first embodiment of the present invention, E designates the eye to be examined, Ef the eye fundus, and C the cornea of the eye. Designated by $11a$, $11b$ and $11c$ are light sources emitting invisible light. These light sources may be, for example, light-emitting diodes emitting infrared rays. Designated by 12 is a mask having three linear slits $12a$, $12b$ and $12c$ equidistant from the center thereof and perpendicular to diametral lines $r_1$, $r_2$, $r_3$ forming 120° with one another, as shown in FIG. 8. The light sources $11a$, $11b$ and $11c$ are disposed behind the slits $12a$, $12b$ and $12c$, respectively. $L_{11}$ designates a first positive movable lens having a focal length of $f_{11}$. Denoted by 13 is a three-aperture stop plate having apertures $13a$, $13b$ and $13c$ equidistant from the center thereof and spaced apart by 120°, as shown in FIG. 9. $L_{12}$ denotes a second positive movable lens having a focal length of $f_{12}$. The first movable lens $L_{11}$ and the second movable lens $L_{12}$ are spaced apart from each other by a distance equal to the sum of their focal lengths $(f_{11}+f_{12})$ and fixed with their optic axis aligned with each other to form an afocal lens group. The three-aperture stop plate 13 is disposed on the common focal plane of the two movable lenses with the center thereof being in line with the optic axis of the afocal lens group. The first and second movable lenses $L_{11}$ and $L_{12}$ and the three-aperture stop plate 13 are made integral with one another and moved in one direction along the optic axis $X_1$ by a driver, not shown, during one measurement. $L_{13}$ designates a positive fixed lens having a focal length of $f_{13}$. Designated by 14 is an apertured mirror having apertures $14a$, $14b$ and $14c$ equidistant from the center thereof and spaced apart by 120°, as shown in FIG. 10. The apertures $14a$, $14b$ and $14c$ have a stop function. This apertured mirror 14 may be replaced by a half-transparent mirror and a three-aperture stop plate, but in that case, there is a reduction in the quantity of light.

The apertured mirror 14 is disposed at the focus position of the fixed lens $L_{13}$ and therefore, if rays having left any of the apertures $14a$, $14b$ and $14c$ are supposed, such rays are collimated by the fixed lens $L_{13}$. Accordingly, even if the afocal lens group ($L_{11}$, 13, $L_{12}$) is moved, the images of the apertures $14a$, $14b$ and $14c$, namely, the size of the pupil, is not varied.

$L_{14}$ designates an objective lens having a positive refractive power, and the optic axis X2 thereof is coincident with the optic axis X1.

Figure 11:
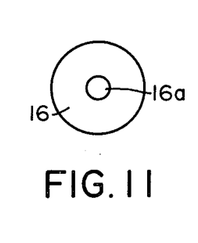

$L'_{13}$ is a fixed lens identical in function with the fixed lens $L_{13}$ and disposed on an optic axis X3. The optic axis X3 is orthogonal to the optic axis X1 on the apertured mirror 14. Denoted by 15 is a mirror for bending the optic axis. $L'_{12}$ designates a movable lens identical in function to the movable lens $L_{12}$. Denoted by 16 is a stop plate having an opening $16a$ centrally thereof, as shown in FIG. 11. $L'_{11}$ is a movable lens identical in function to the movable lens $L_{11}$. The movable lens $L'_{12}$ and the movable lens $L'_{11}$ are spaced apart from each other by the sum of their focal lengths and form an afocal lens group. The stop plate 16 is disposed on the common focal plane of the movable lenses $L'_{12}$ and $L'_{11}$, and these are integrally movable on the optic axis X3.

Figure 12:
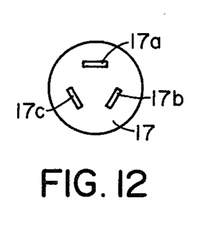

Designated by 17 is a light-receiving mask having slits $17a$, $17b$ and $17c$ as shown in FIG. 12, and slits $12a$ and $17a$, $12b$ and $17b$, and $12c$ and $17c$ are in optically conjugate relation. Denoted by $18a$, $18b$ and $18c$ are light receptors which can substantially cover the slit opening portions of the slits $17a$, $17b$ and $17c$.

On the other hand, if the apertures of the apertured mirror 14 are conjugate with the front portion (cornea C or iris) of the eye to be examined when the operating distance between the objective lens $L_{14}$ and the eye E is proper, this cornea surface or iris surface acts as the exit pupil of the eye and this pupil has the same relation as the apertures of the apertured mirror 14 with respect to the fixed lenses $L_{13}$, $L_{13}'$ and the afocal lens group, and accordingly, has an afocal relation and therefore, the dimensions of the pupil are not varied.

Also, the three-aperture stop plate 13 is always conjugate with the apertured mirror 14 and therefore, the cornea C conjugate with the apertured mirror 14 is also conjugate with the three-aperture stop plate 13. Accordingly, the beams having passed through the apertures $13a$, $13b$ and $13c$ of the three-aperture plate 13 are separated from one another on the cornea. The stop plate 16 is likewise always conjugate with the cornea C and limits the outer edge of the beam exiting from the eye to be examined.

The light sources $11a$, $11b$ and $11c$ should preferably be of strong directionality so that the beams having left the slits $12a$, $12b$ and $12c$ of the mask enter only into a particular aperture of the apertured mirror 14.

The operation of this embodiment will now be described. In this embodiment, the refractive powers in at least three diametral line directions are measured at a time and therefore, the three light sources 11a, 11b, 11c and the three light receptors 18a, 18b, 18c are operated at a time, but for convenience of description, only the light source 11a and light receptor 18a will be explained. When the light source 11a is turned on, the slit 12a of the mask 12 is illuminated by infrared light. The beam having left the slit 12a passes through the first movable lens $L_{11}$, the aperture 13a of the three-aperture stop plate 13, the second movable lens $L_{12}$, the fixed lens $L_{13}$ and the aperture 14a of the apertured mirror 14 and once forms the image of the slit 12a, and further passes through the objective lens $L_{14}$ into the eye E to form the image of the slit 12a on the eye fundus Ef. The beam reflected by the eye fundus Ef exits from the eye E and is once imaged by the action of the objective lens $L_{14}$, and then reflected by the mirror surface of the apertured mirror 14 and enters the fixed lens $L'_{13}$ and is reflected by the mirror 15, whereafter the beam passes through the movable lens $L'_{12}$, the opening 16a of the stop plate 16 and the movable lens $L'_{11}$ to form the image of the slit 12a on the light-receiving mask 17. Only the beam which has passed through the slit 17a of the light-receiving mask 17 enters the light receptor 18a.

Where the eye to be examined has an abnormal refractive power, the eye fundus exhibits such a behavior that it has apparently moved to the position of Ef', for example, but when the movable lens group $L_{11}$, the three-aperture stop plate 13 and the movable lens $L_{12}$ are moved simultaneously with the movable lens $L_{11}'$, the three-aperture stop 13 and the movable lens $L_{12}$, the mask 12 and the surface Ef' corresponding to the eye fundus become conjugate somewhere in the range of movement and accordingly, the mask 17 also becomes conjugate and therefore, the light receptors 18a, 18b and 18c detect the extremal value. Where the eye to be examined has astigmatism, the light receptors detect the extremal value at different points of time. Also, before and after the mask and the eye fundus become conjugate, the images of the slits 12a, 12b, 12c formed on the mask 17 are blurred and deviated in the diametral line direction and therefore, the quantity of light incident on the light receptors is decreased.

As described above, if the afocal lens group $L_{11}$, $L_{12}'$ and the other afocal lens group $L'_{11}$, $L'_{12}$ are moved at a time in the direction of the optic axis, the mask 12 and the eye fundus Ef' become conjugate and, when the eye fundus Ef' and the light-receiving mask 17 have become conjugate, the light receptors 18a, 18b and 18c produce their maximum outputs and therefore, if that position of the afocal lens group is detected, the diopter value of the eye to be examined can be calculated from the following equation:

$$l = \frac{(f_{13})^2 \cdot (f_{11})^2}{100 \{(f_{12})^2 - (f_{11})^2\}} \cdot D_7$$

where D is the unknown diopter value of the eye to be examined, and l is the amount of movement of the afocal lens group effected for the focusing from the standard position occupied by the afocal lens group when the diopter was zero.

Figure 13:
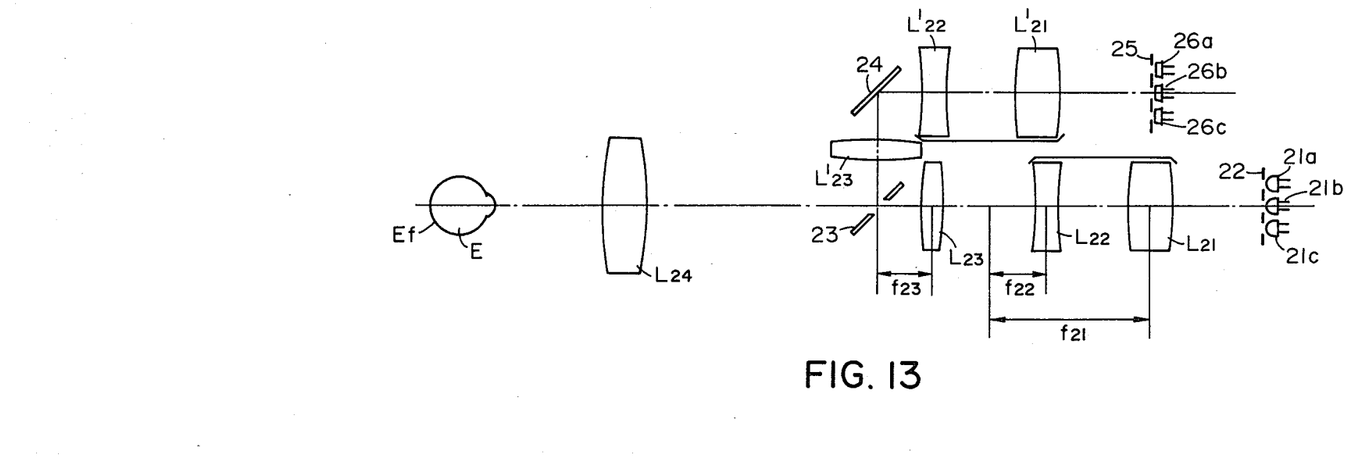
FIG. 13 is a longitudinal cross-sectional view of a second embodiment of the present invention.
Figure 14:
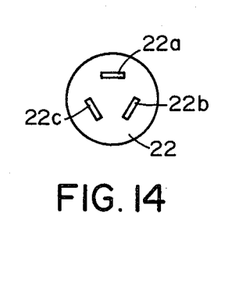
FIGS. 14–16 are plan views of the components in the embodiment of FIG. 13.
Figure 15:
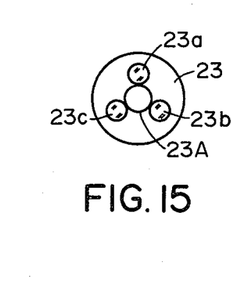

FIG. 13 shows a second embodiment of the present invention. In FIG. 13, reference characters 21a, 21b and 21c designate light sources, and reference numeral 22 denotes a mask having three slits 22a, 22b and 22c as shown in FIG. 14. The mask 22 is similar to the mask 12 of FIG. 8. $L_{21}$ denotes a positive movable lens having a focal length of $f_{21}$, and $L_{22}$ designates a negative movable lens having a focal length of $f_{22}$ and having the focus position thereof coincident with the focus position of the lens $L_{21}$. Accordingly, the lens $L_{21}$ and the lens $L_{22}$ together constitute an afocal system and these two lenses are movable as a unit in the direction of the optic axis. $L_{23}$ designates a positive fixed lens having a focal length of $f_{23}$. Denoted by 23 is an apertured mirror having three reflecting portions 23a, 23b and 23c equidistant from the center thereof and spaced apart from one another by 120°, and further having an opening 23A at the center thereof. This apertured mirror 23 is disposed at the focus position of the fixed lens $L_{23}$. $L_{24}$ designates an objective lens, and $L'_{23}$ designates a fixed lens similar to the fixed lens $L_{23}$ and disposed at a position spaced apart from the apertured mirror 23 by the focal length $f_{23}$. Denoted by 24 is a mirror for bending the optical path. $L_{21}'$ is a lens equivalent to the movable lens $L_{21}$, and $L_{22}'$ is a lens equivalent to the movable lens $L_{22}$, and these lenses are held at an interval with their focuses being likewise coincident with each other, and are movable as a unit and with the lenses $L_{21}$ and $L_{22}$ in the direction of the optic axis.

The lenses $L_{21}$ and $L_{22}$ and the lenses $L_{21}'$ and $L_{22}'$ are in afocal relation with the apertured mirror and accodingly, are in afocal relation with the exit pupil of the eye to be examined.

Figure 16:
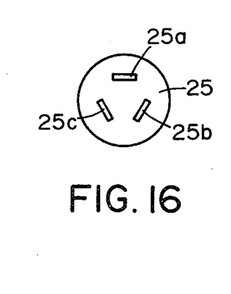

Designated by 25 is a light-receiving mask having slits 25a, 25b and 25c as shown in FIG. 16. This light-receiving mask 25 is similar to the light-receiving mask 17 of FIG. 12. Denoted by 26a, 22b and 26c are light-receptors for receiving the light which enters the slits 25a, 25b and 25c. The light from the light source 21a passes through the slit 22a, the positive movable lens $L_{21}$, the negative movable lens $L_{22}$, the aperture 23A of the apertured mirror 23 and the objective lens $L_{24}$ to the eye fundus Ef of the eye E to be examined. The light reflected from the eye fundus Ef passes to the slit 25a of the light-receiving mask 25 via the objective lens $L_{24}$, the reflecting portion 23a of the apertured mirror 23, the fixed lens $L_{23}'$, the reflecting member 24, the negative movable lens $L_{22}'$ and the positive movable lens $L_{21}'$, and is received by the light receptor 26a. This also holds true with the lights from the light sources 21b and 21c.

Figure 17:
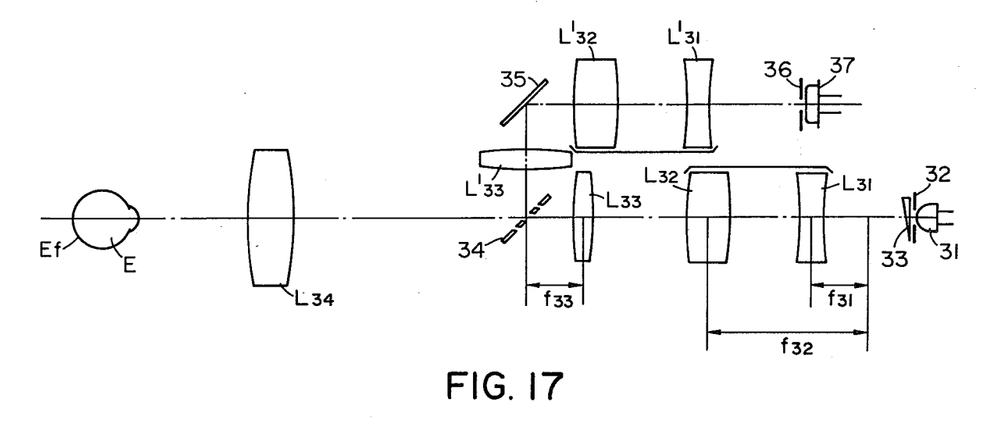
FIG. 17 is a longitudinal cross-sectional view of a third embodiment of the present invention.
Figure 18:
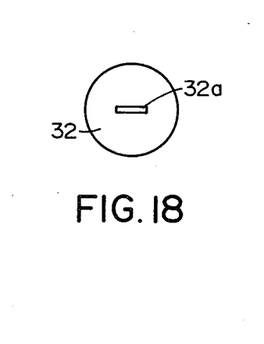
FIGS. 18, 19 and 20 are plan views of the components in the embodiment of FIG. 17.
Figure 19:
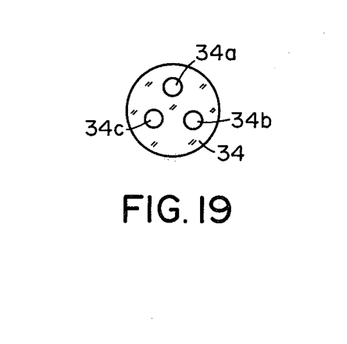

FIG. 17 shows a third embodiment of the present invention. Designated by 31 is a light source, and denoted by 32 is a mask having a slit 32a as shown in FIG. 18. Designated by 33 is a triangular prism pillar having a refracting power in the direction of the shorter sides of the slit 32a. The mask 32 and the prism pillar 33 are integrally rotated about the optic axis and, when the longer sides of the slit 32a have become perpendicular to three predetermined meridians, the light source 31 is turned on. The light-receiving mask 36 is rotatable about the optic axis in synchronism with the mask 32.

Figure 20:
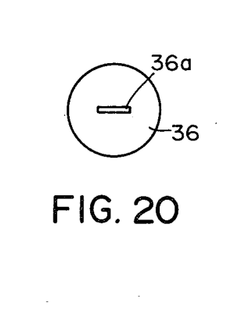

$L_{32}$ designates a positive movable lens having a focal length of $f_{32}$ and having its focus position coincident with the focus position of the lens $L_{31}$. Moreover, lenses $L_{31}$ and $L_{32}$ are integral. Denoted by $L_{33}$ is a fixed lens having a focal length of $f_{33}$ and having its focus position at the position of an apertured mirror to be described. Denoted by 34 is an apertured mirror having three apertures 34a, 34b and 34c equidistant from the center thereof and spaced apart from one another by 120°. $L_{34}$ denotes an objective lens, E the eye to be examined, Ef the eye fundus, $L_{33}'$ a fixed lens similar to $L_{33}$ and disposed at a position conjugate with $L_{33}$ with respect to the apertured mirror 34, 35 a reflecting member, $L_{32}'$ a positive movable lens similar to $L_{32}$ and disposed at a position conjugate with $L_{32}$ with respect to the apertured mirror 34, $L_{31}'$ a negative movable lens similar to $L_{31}$ and disposed at a position conjugate with $L_{31}$ with respect to the apertured mirror 34, 36 a light-receiving mask having a slit 36a conjugate with the eye fundus image of the slit 32a as shown in FIG. 20, and 37 a light receptor for receiving the light of the light-receiving mask. The mask 32, the triangular prism pillar 33 and the light-receiving mask 36 are rotatable about the optic axis and, when the shorter side direction of the slit 36a of the mask 36 has become coincident with the direction of the three apertures 34a, 34b and 34c of the apertured mirror 34, the light source 31 is turned on. The speed is such a degree of high speed that the variation is refractive power induced by the movement of the movable lens during this flicker period becomes lower than the resolving power.

In the above-described embodiments, the same optical systems are used on the light source side and on the light receptor side with the apertured mirror as the boundary, whereas the same optical systems need not be used if the amount of movement of the optical systems is varied.

Figure 21:
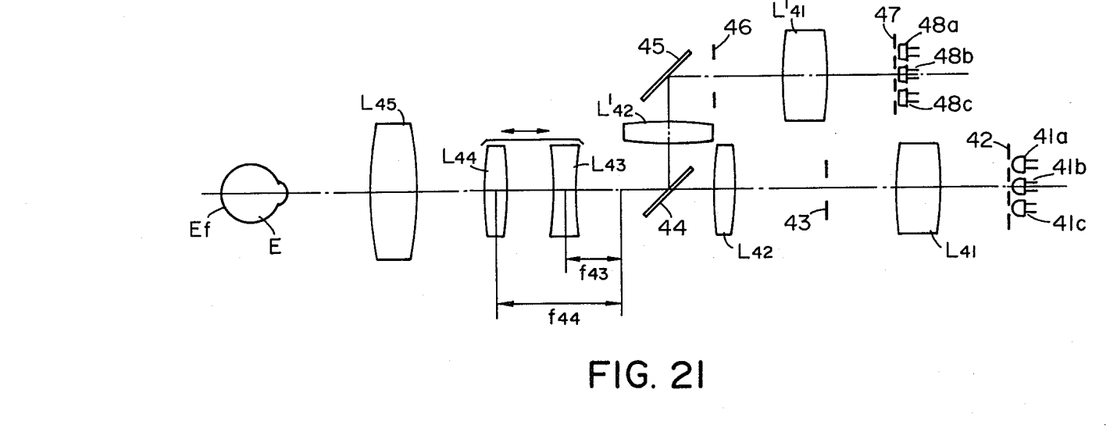
FIG. 21 is a longitudinal cross-sectional view of fourth embodiment of the present invention.
Figure 22:
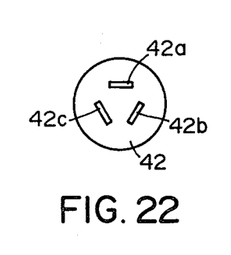
Figure 23:
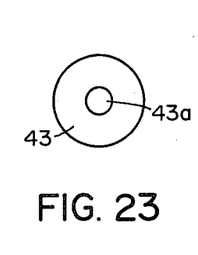
Figure 24:
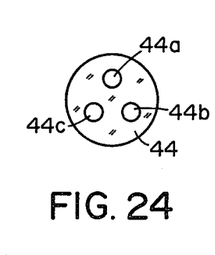

FIG. 21 shows a fourth embodiment of the present invention. Designated by 41a, 41b and 41c are light sources. Reference numeral 42 designates a mask having three slits 42a, 42b and 42c equidistant from the center thereof and spaced apart from one another by 120°, $L_{41}$ a fixed lens, 43 an aperture stop having an opening 43a as shown in FIG. 23 and disposed at the image forming position of a fixed lens $L_{42}$ to be described, 42 a fixed lens, 44 an apertured mirror having apertures 44a, 44b and 44c equidistant from the center thereof and spaced apart from one another by 120°, $L_{43}$ a negative movable lens having a focal length of $f_{43}$, and $L_{44}$ a positive movable lens having a focal length of $f_{44}$ and having its focus position coincident with the focus position of the lens $L_{43}$. The lens $L_{44}$ is movable with the lens $L_{42}$. $L_{45}$ denotes an objective lens whose focal plane is coincident with the pupil of the eye to be examined when the distance between the objective lens and the eye E is an optimum operating distance.

Figure 25A:
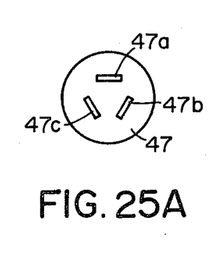
Figure 25B:
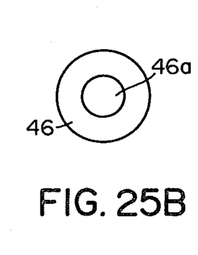

$L_{42}'$ designates a fixed lens similar to $L_{42}$ and disposed at a position conjugate with the fixed lens $L_{42}$ with respect to the apertured mirror 44, 45 a reflecting member, 46 an aperture stop disposed at a position conjugate with the aperture stop 43 with respect to the apertured mirror 44 and having an opening 44a as shown in FIG. 25B, $L_{41}'$ a lens similar to $L_{41}$ and disposed at a position conjugate with the fixed lens $L_{41}$ with respect to the apertured mirror 44, and 47 a light receiving mask as shown in FIG. 25A. The slits 42a, 42b, 42c and the slits 47a, 47b, 47c are conjugate with each other with respect to the eye fundus. Designated by 48a, 48b and 48c are light receptors whose light-receiving surfaces cover the slits 47a, 47b and 47c, respectively.

In the above-described apparatus, when the afocal lens group $L_{43}$, $L_{44}$ is moved on the optic axis in one direction, the light receptors 48a, 48b and 48c detect the extremal value in the course of movement of the afocal lens group and therefore, from that position of the afocal lens group on the optic axis, it is possible to measure the refractive power in each diametral line direction.

Figure 26:
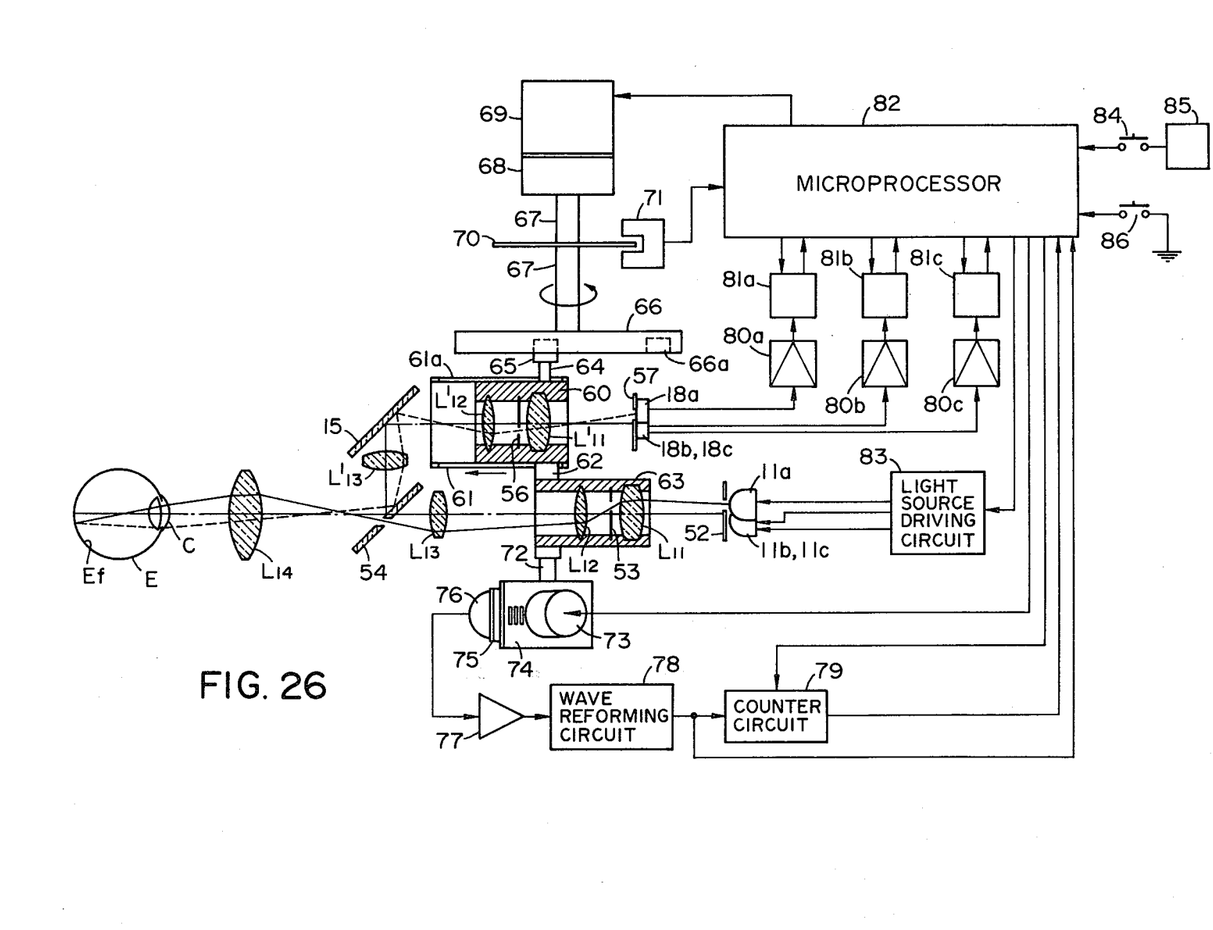
FIG. 26 is a view of a fifth embodiment of the present invention in which the optical system and the electric circuit are coupled together.
Figure 27:
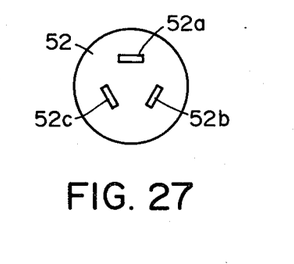
FIGS. 27–32 are plan views of the components in the embodiment of FIG. 26.
Figure 28:
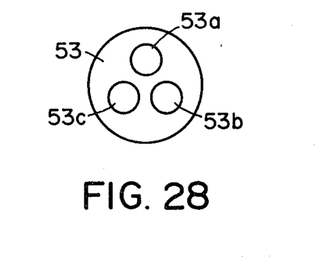
Figure 29:
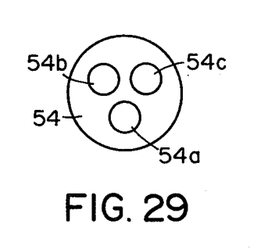

FIG. 26 shows the entire system including a signal processing system. In this Figure, the movable lenses $L_{11}$ and $L_{12}$, the fixed lens $L_{13}$ and the objective lens $L_{14}$, the fixed lens $L_{13}'$, and the movable lenses $L_{11}'$ and $L_{12}'$ are equivalent to the lenses of FIG. 7 and disposed in a relation similar to that in FIG. 7. Designated by 11a, 11b and 11c are infrared light emitting diodes providing light sources and their flicker period is set so that the variation in refractive power induced by the movement of the movable lens becomes lower than the resolving power. Denoted by 52 is a mask having three linear slits 52a, 52b and 52c equidistant from the center thereof and perpendicular to the diametral line, as shown in FIG. 27. Denoted by 53 is a three-aperture stop having three apertures 53a, 53b and 53c equidistant from the center thereof and corresponding to diametral lines forming 120° with one another, as shown in FIG. 28. The focuses of the movable lenses $L_{11}$ and $L_{12}$ are coincident with the three-aperture stop. Denoted by 54 is an apertured mirror having apertures 54a, 54b and 54c equidistant from the center thereof and corresponding to the diametral lines spaced apart from one another by 120°. Designated by 15 is a mirror for bending the optical path.

Figure 30:
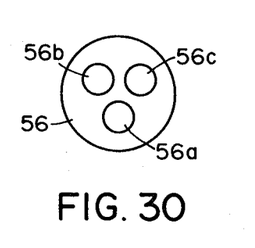

Denoted by 56 is a three-aperture stop having three apertures 56a, 56b and 56c equidistant from the center thereof and spaced apart from one another by 120°, as shown in FIG. 30. The apertures of the three-aperture stop 56 are optically symmetric with the apertures 54a, 54b and 54c of the apertured mirror 54 with respect to the optic axis. This three-aperture stop 56 lies at the focus position of the movable lenses $L_{11}'$ and $L_{12}'$.

Figure 31:
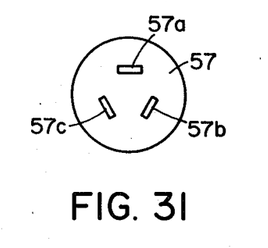

Designated by 57 is a light-receiving mask having slits 57a, 57b and 57c, as shown in FIG. 31. The slits 52a and 57a, 52b and 57b, and 52c and 57c are in optically conjugate relation. Denoted by 18a, 18b and 18c are light receptors which can substantially cover the slits 57a, 57b and 57c, respectively. The light from the light source 11a passes through the slit 52a, the movable lens $L_{11}$, the aperture 53a of the three-aperture stop 53, the movable lens $L_{12}$, the fixed lens $L_{13}$, the aperture 54a of the apertured mirror 54, the objective lens $L_{14}$ and the cornea C to the eye fundus Ef of the eye E to be examined and forms the image of the slit 52a. The light reflected by the eye fundus Ef passes to the slit 57a on the light-receiving mask 57 via the cornea C, the objective lens $L_{14}$, the apertured mirror 54, the fixed lens $L_{13}'$, the reflecting member 15, the movable lens $L_{12}'$, the aperture 56a of the aperture stop 56 and the movable lens $L_{11}'$ and is received by the light receptor 18a. This also holds true with the lights from the light sources 11b and 11c. When the diopter of the eye to be examined has been varied, the eye fundus reflected images of the slits 52a, 52b and 52c move on the slit 57 radially of the slits 57a, 57b and 57c, so that the quantity of light entering the light receptors fluctuates.

Designated by 60 is a support member supporting the movable lenses $L_{11}'$ and $L_{12}'$ and the three-aperture stop 56. The support member 60 is inscribed to the inner side of a drum 61 for guiding in the direction of the optic axis and is slidable in the direction of the optic axis. Denoted by 63 is a member supporting the movable lenses $L_{11}$ and $L_{12}$ and the three-aperture stop 53. The member 63 is fixed parallel to the support member 60 by a connecting member. Designated by 64 is a coupling member projecting from the support member 60 and having a roller 65 fitted on the end thereof. A guide drum 61 has a long groove 61a extending in the direction of the optic axis, and the width of the groove is such that the guide drum loosely fits to the coupling member to prevent the support members 60 and 63 from rotating about the optic axis. Designated by 66 is a cam plate having in the side thereof a cam groove 66a of such a width as to fit to the roller 65. The cam plate 66 is fixed to a rotary shaft 67.

Figure 32:
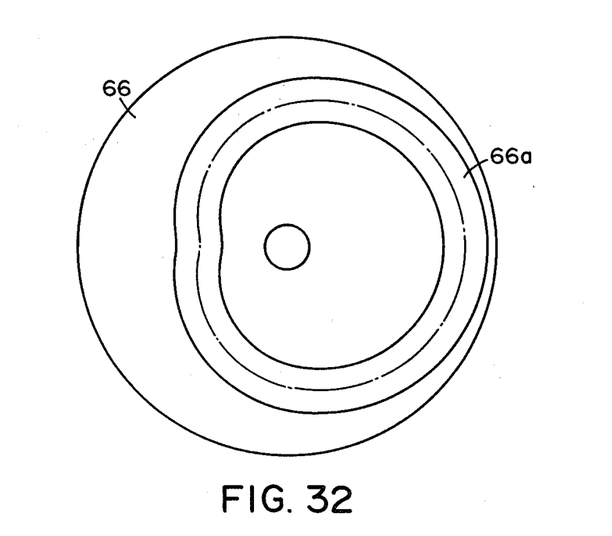

A plan view of the cam plate 66 is shown in FIG. 32. The cam groove 66a adopts a straight line as the basic curve of the cam diagram, and the amount of displacement of followers 63, 64 for the rotational angle of the cam is made constant. The rotary shaft 67 is supported by a bearing, not shown. Reference numeral 68 designates a gear head, and reference numeral 69 denotes a motor.

The motor 69 is a motor of the one-way rotation type designed so as to be stably rotated at a constant speed by a rotation irregularity controller such as, for example, a tacho-generator. By the motor rotating at a constant speed and the cam adopting a straight line as the basic curve, the amount of movement per unit time of the movable lens is made constant and since the amount of movement of the movable lens and the refractive power are in the relation of 1:1, the variation in refractive power becomes constant.

The gear head 68 has its reduction ratio set so that the cam plate 66 assumes a predetermined number of revolutions. When the cam plate is rotated, it forces out the roller 65 in the direction of the roller 65 to move the movable lens in the direction of the optic axis.

Designated by 70 is a disc having a sector cut-away in the outer edge portion thereof. The disc 70 is fixed to the rotary shaft 67 and has the function of opening and closing the optical path between the light-emitting portion and light-receiving portion of a photoelectric switch to detect the angular position of the cam plate 66, and the output thereof is applied to a microprocessor 82 at TTL level.

The microprocessor 82 comprises a CPU, memory elements (ROM, RAM), an input control circuit, a clock, etc., and is programmed so as to effect the intensive control, sequence control, function operating process and display control of a signal processing circuit to be described.

The disc 70 and photoelectric switch 71 are provided for detecting the effective section of the input of refraction measurement data to the microprocessor, and the disc 70 is provided with a sector cut-away which enables the section except the opposite ends, as long as about 0.5 mm, of the forward path of the reciprocal movement from a point about 0.5 mm past the position whereat the movable lens is closest to the mask 52, in the direction of arrow, to a point about 0.5 mm short of the position whereat the movable lens is closest to the apertured mirror 54 to be identified as the effective section, and the identification signal is applied to the microprocessor to effect the resetting of a counter circuit 79.

Members 73 to 79 constitute a photoelectric type linear encoder for detecting the amount of movement of the movable lens. Reference character 73 designates a light source, and reference character 74 denotes a glass scale having a number of light transmitting slits. The glass scale 74 is fixed to a connecting member 62 by a connecting member 72 and movable in the direction of the optic axis equally to the movement of the movable lens. Reference numeral 75 designates a glass mask having a light transmitting slit. Reference numeral 76 denotes a light-receiving element whose output is applied to an amplifier 77. Reference numeral 78 designates a wave reforming circuit, and reference numeral 79 denotes a counter circuit which counts pulses to thereby detect the amount of movement of the movable lens and applies the detection signal to the microprocessor 82. The ratio between the amount of movement of the movable lens and the variation in refractive power is constant irrespective of the refractive power of the object and therefore, if the pitch of the light transmitting slits of the glass scale 74 is set, for example, to a dimension corresponding to 0.25 diopter, a pulse for each 0.25 diopter will be applied to the microprocessor 82 with the movement of the movable lens.

Designated by 83 is a light source driving circuit having the function of turning on and off the light source at a much higher speed than the speed of movement of the movable lens.

Designated by 80a is an amplifier for demodulating only the quantity-of-light signal superimposed upon a carrier wave from the output of the light receptor 18a. The amplifier 80a comprises a pre-amplifier, a band-pass filter and a demodulator for detecting a signal wave. The demodulation output signal is delivered to an A/D converter 81a, by which it is converted into a digital signal in synchronism with the pulse put out by the linear encoder and is delivered to the microprocessor for storage therein. The microprocessor 82 immediately reads out its stored digital value and compares it with the digital signal A/D-converted by the A/D converter 81a, in response to the next pulse signal. The input from the A/D converter 81a is compared with the digital value A/D-converted and stored in response to the immediately earlier pulse and, when the former is greater than the latter, the comparison is repeated to eliminate the former and cause the latter to be stored and, at a point of time whereat the former has become smaller than the latter, an instruction for causing the output of the counter circuit 79 to be stored is put out to cause the memory to store said output and stop the comparison, thus inhibiting the input from the A/D converter 81a. Also, the microprocessor is programmed to convert the output of the counter circuit into visibility and to convert the stored value into a visibility value and correct it to the visibility value earlier by one pulse. The visibility value thus obtained is the maximum value obtained during one measurement, and is the spherical surface visibility in a diametral line of the eye to be examined, and this is stored in the memory. Elements 80b and 81b process the output from 18b and elements 80c and 81c likewise process the output from 18c, and these store the spherical surface visibilities in the other two diametral lines of the eye to be examined.

Next, when the spherical surface visibilities in the three diametral lines of the eye to be examined are stored, the microprocessor stops the function of each A/D converter.

Reference numeral 84 designates a power source switch, 85 a power source and 86 a measuring switch.

In the above-described construction, when the power source switch 84 is closed, the motor 69 is supplied with electric power in accordance with the instruction of the microprocessor 82 and the cam plate 66 is rotated to reciprocally move the movable lens in the direction of the optic axis and, after the rising time of the motor 69, the movable lens is moved at a constant speed. The photoelectric switch 71 is also supplied with electric power to apply the effective measurement section detection signal to the microprocessor.

After having closed the power source switch, the examiner causes the examinee to take a predetermined position, adjusts the objective lens of the refractometer to the eye E to be examined, causes the examinee to watch a fixed target, not shown, and closes the measuring switch 86. The microprocessor receives the input of the measuring switch 86 to operate the light source driving circuit 83 and turn on the light sources 11a, 11b and 11c and supplies each circuit with a predetermined electric power to operate each circuit. The lights from the light sources 11a, 11b and 11c pass through the aforementioned path to the slits 57a, 57b and 57c, respectively, on the light-receiving mask 57 and are received by the light receptors 18a, 18b and 18c. Also, the microprocessor examines whether or not the movable lens is positioned in the effective measurement section, by the output of the photoelectric switch 71 when the measuring switch 86 has been closed, and resets the counter circuit 79 by the inversion of the output sign of the photoelectric switch 71 when the movable lens has come into the effective measurement section from outside of the effective measurement section, and applies to the A/D converters 80a, 80b and 80c the unit visibility generated by the photoelectric type linear encoder, for example, the pulse for each 0.25 diopter, and the outputs from the light receptors 18a, 18b and 18c amplified by the amplifiers 81a, 81b and 81c are successively digitalized and applied to the microprocessor. Then, storage, read-out and comparison of the input from the counter circuit and the digitalized output from each light receptor is repeated as already described and, when the movable lens is further moved and the outputs of the light receptors 18a, 18b and 18 c assume their respective maximum values, the microprocessor causes the respective visibility values to be stored and inhibits the inputs from the A/D converters, thus completing the introduction of data.

When the relay lens is further moved and passes the effective section, the output sign of the photoelectric switch 71 is inverted and the microprocessor calls out the stored visibility which has assumed the maximum value of the three diametral lines and starts the function operating process to calculate the spherical surface visibility, the degree of astigmatism and the astigmatism axis angle and causes the results to be digitally displayed on a display device, not shown. Also, the microprocessor causes the light emission of the light sources to be stopped by the output sign inverted signal of the above-described photoelectric switch 71.

What we claim is:

1. An apparatus for measuring the refractive power of the eye comprising:
   generating means for generating radiant energy;
   a first optical system for directing said radiant energy to the eye to be examined, said first optical system having fixed optical means and first afocal optical means movable in the direction of the optic axis;
   a second optical system for receiving the radiant energy reflected by the eye fundus of said eye, said second optical system having second afocal optical means movable in the direction of the optic axis;
   detecting means for detecting the radiant energy passed through said second optical system;
   coupling means for coupling said first optical system and said second optical system;
   driving means for driving said first and second afocal optical means; and
   position detecting means for detecting the position of one of said first and second afocal optical means on the optic axis.

2. The apparatus according to claim 1, wherein said first and second afocal optical means respectively comprise two lens groups having the focal planes thereof overlapped with each other.

3. The apparatus according to claim 2, wherein said lens groups respectively have a positive refractive power.

4. The apparatus according to claim 2, wherein said lens groups comprise a lens group having a positive refractive power and a lens group having a negative refractive power.

5. The apparatus according to claim 1, wherein at least one of said first and second afocal optical means comprises two lens groups having the focal planes thereof overlapped with each other, and means for limiting said radiant energy disposed at said focal planes.

6. The apparatus according to claim 5, wherein said means for limiting said radiant energy has a plurality of apertures.

7. The apparatus according to claim 5, wherein said means for limiting said radiant energy has an aperture.

8. An apparatus for measuring the refractive power of the eye, comprising:
   generating means for generating radiant energy;
   an optical system for directing said radiant energy to the eye to be examined and receiving the radiant energy reflected by the eye fundus of said eye, said optical system having fixed optical means and afocal optical means movable in the direction of the optic axis;
   detecting means for detecting the radiant energy passed through said optical system;
   driving means for driving said afocal optical means;
   position detecting means for detecting the position of said afocal optical means on the optic axis; and
   means for dividing the main optical path of said optical system into first and second optical paths, with said generating means being disposed in said first optical path and said detecting means being disposed in said second optical path.

9. The apparatus according to claim 8, wherein said afocal optical means comprises two lens groups having the focal planes thereof overlapped with each other.

10. The apparatus according to claim 9, wherein said lens groups comprise a lens group having a positive refractive power and a lens group having a negative refractive power.

11. The apparatus according to claim 1 or 8, wherein said generating means has a mask having a measuring chart, and illuminating means for illuminating said mask.

12. The apparatus according to claim 11, wherein said measuring chart comprises slits corresponding to at least three diametral lines.

13. The apparatus according to claim 11, wherein said generating means further has a prism rotatable about the optic axis.

14. The apparatus according to claim 11, wherein said illuminating means intermittently illuminates said mask.

15. The apparatus according to claim 1 or 8, wherein said fixed optical means is a lens having a positive refractive power.

16. The apparatus according to claim 1 or 8, wherein said detecting means comprises a mask provided with a plurality of openings, and a plurality of photocells disposed behind said mask.

17. An apparatus for measuring the refractive power of the eye comprising:
an objective lens for directing light energy to the eye to be examined and receiving the light energy from the eye fundus;
an apertured mirror disposed rearwardly of said objective lens and forming a first optical path and a second optical path;
a first fixed lens disposed on said first optical path so that said apertured mirror and the focal plane of said first fixed lens are substantially coincident with each other;
a first afocal lens group disposed on said first optical path rearwardly of said first fixed lens and movable in the direction of the optic axis;
a first mask disposed on said first optical path rearwardly of said first afocal lens group and having a section through which said light energy passes;
a source for illuminating said first mask with light energy;
a second fixed lens disposed on said second optical path so that said apertured mirror and the focal plane of said second fixed lens are substantially coincident with each other;
a second afocal lens group disposed on said second optical path rearwardly of said second fixed lens and movable in the direction of the optic axis;
a second mask disposed on said second optical path rearwardly of said second afocal lens group and having a section through which said light energy passes;
light-receiving means for receiving the light energy passed through said second mask and generating a first signal;
driving means for driving said first and second afocal lens groups;
position detecting means for detecting the position of one of said first and second afocal lens groups on the optic axis and generating a second signal; and
calculating means for calculating the refractive power of the eye from said first and second signals.

18. The apparatus according to claim 17, wherein said first and second afocal lens groups respectively have two sub-groups.

19. The apparatus according to claim 18, wherein said sub-groups both have a positive refractive power.

20. The apparatus according to claim 18, wherein one of said sub-groups has a positive refractive power and the other has a negative refractive power.

21. The apparatus according to claim 17, wherein said first and second afocal lens groups respectively comprise two sub-groups having the focal planes thereof coincident with each other, and limiting means for limiting the light energy disposed on said focal planes.

22. The apparatus according to claim 17, wherein said light energy is infrared light.

* * * * *